| United States Patent [19] | [11] Patent Number: 5,002,773 |
| Keshary et al. | [45] Date of Patent: Mar. 26, 1991 |

[54] TRANSDERMAL DELIVERY OF (+) (2S,3S)-3-ACETOXY-8-CHLORO-5-(2-DIMETHYLAMINOETHYL)-2,3-DIHYDRO-2-(4-METHOXYPHENYL)-1,5-BENZOTHIAZEPIN-4-(5H)-ONE

[75] Inventors: Prakash R. Keshary, Lenexa, Kans.; Donna R. Jones, Harrisonville, Mo.; James W. Mitchell, Leawood, Kans.

[73] Assignee: Marion Merrell Dow Inc., Kansas City, Mo.

[21] Appl. No.: 414,381

[22] Filed: Sep. 29, 1989

[51] Int. Cl.$^5$ .............................................. A61F 13/02
[52] U.S. Cl. ...................................... 424/448; 424/449
[58] Field of Search ................................ 424/449, 448

[56] References Cited

U.S. PATENT DOCUMENTS 4,777,047 10/1988 Bauer et al. ........................ 424/445
4,879,289 11/1989 Zobrist et al. ...................... 514/211

*Primary Examiner*—Thurman K. Page
*Assistant Examiner*—L. Horne
*Attorney, Agent, or Firm*—Theresa M. Gillis

[57] ABSTRACT

A method for treating angina, epilepsy and hypertension by achieving vasodilation, anti-angina or anti-convulsant effect in a patient is described. The method involves transdermally administering to a patient in need of vasodilation or anti-convulsant effect the compound known as (+)(2S,3S)-acetoxy-8-chloro-5-(2-dimethylaminoethyl)-2,3-dihydro-2-(4-methoxyphenyl)-1,5-benzothiazepin-4-(5H)-one in an amount sufficient to achieve desired systemic vasodilation, anti-angina or anti-convulsant levels of the compound.

5 Claims, No Drawings

TRANSDERMAL DELIVERY OF (+) (2S,3S)-3-ACETOXY-8-CHLORO-5-(2-DIMETHYLAMINOETHYL)-2,3-DIHYDRO-2-(4-METHOXYPHENYL)-1,5-BENZOTHIAZEPIN-4-(5H)-ONE

BACKGROUND OF THE INVENTION (a) Field of Invention

The invention relates to the use of transdermal delivery devices for controlled administration through the skin of benzothiazepine calcium antagonists to maintain a sustained systemic therapeutic amount of the drug for an extended period of time in a patient. More particularly, the invention relates to transdermal administration of (+)(2S,3S)-3-acetoxy-8-chloro-5-(2-dimethylaminoethyl)-2,3-dihydro-2-(4-methoxyphenyl)-1,5-benzothiazepin-4-(5H)-one for treatment of diseases such as hypertension, angina and convulsions.

(b) State of the Art

Pharmaceutically active drugs are commonly administered to patients in need of treatment in periodic doses given orally or by injection to maintain adequate systemic therapeutic levels of the drug. For a variety of reasons, it is often advantageous to administer certain drugs, e.g. drugs which act on the cardiovascular system, in a single daily oral or injected sustained release dose. However, many drugs are not efficiently administered in such a single daily dosage regimen, because of incomplete absorption from the gastrointestinal tract and/or so-called first-pass metabolism by the liver.

As a result of these problems, techniques for administering drugs by absorption through the skin to afford sustained systemic levels in a patient have been developed. In accordance with these techniques, transdermal delivery devices have been developed which administer a wide variety of drugs, including hormones, antibiotics, vasoactive drugs and others. Transdermal devices for administering nitroglycerine and scopolamine are commercially available at present.

In a transdermal device, the drug is commonly incorporated into a polymeric reservoir material, such as a silicone elastomer or acrylic polymer matrix, for controllable release of the drug through the skin. See, e.g., U.S. Pat. Nos. 3,996,934 and 4,460,371 which teach such devices. The device also has means by which it may be affixed to the skin of the patient for delivery of the drug. Experimentation to determine which delivery system is best for a particular drug is often required, however, because it is well known that a particular transdermal delivery system which is useful with one drug, may not be useful with others.

Moreover, as disclosed in U.S. Pat. No. 4,615,699, incorporation of permeation enhancers into the transdermal delivery system is often required to potentiate or enhance permeation of the drug through the skin to obtain effective serum levels. For example, U.S. Pat. No. 4,645,502 teaches a transdermal delivery device for efficient delivery of highly ionized fat insoluble drugs, including the ionized forms (i.e., salts) of various drugs. The invention is premised on the observation that unionized forms of most drugs are more permeable through skin than their ionized forms, i.e., generally the salt of a particular drug cannot be delivered through the skin, absent some way of enhancing permeation. The '502 patent provides such a transdermal delivery device which incorporates a permeation enhancer element to achieve efficient permeation of ionized drugs through the skin.

Transdermal delivery of vasodilator drugs, primarily nitroglycerine, and other cardiovascular drugs such as beta receptor antagonists (e.g., propranolol) and cardiac glycosides (e.g., digoxin) is particularly attractive as a means of maintaining sustained levels of such drugs in a patient. A variety of devices for delivering such drugs has been developed. See e.g., U.S. Pat. Nos. 4,460,562, 4,573,996 and 4,668,232 and published European Application No. 0159168.

Calcium antagonists are an important group of vasodilators which have found wide clinical use in the treatment of cardiovascular problems, such as angina and hypertension. Chemically, calcium antagonists form a diverse group of organic compounds, all of which inhibit the flux of calcium ions through calcium channels in cell membranes. Four chemical classes of calcium antagonists are generally recognized: (1) the dihydropyridines, exemplified by nifedipine and nimodipine; (2) the phenylalkylamines, such as verapamil; (3) the diphenylalkylamines, such as flunarizine and (4) the benzothiazepines, such as diltiazem. Generally, such drugs are orally administered to a patient, often in several doses per day to maintain adequate therapeutic levels. A once a day sustained release dosage, if feasible, would be preferable for these drugs, however.

Various devices which can provide transdermal delivery of calcium antagonists have been developed. For example, U.S. Pat. No. 4,637,930 discloses transdermal delivery of nicardipine hydrochloride, which has both cerebral and coronary vasodilating properties. Because of the drug's poor permeability through skin, however, the '930 patent teaches that permeability enhancers, including propylene glycol, 2-4 carbon monohydric alcohols, thioglycol, 6-12 carbon mono- and di-fatty acid esters of glycerol, 6-12 carbon mono- and di-fatty acid esters of sorbitol and urea, must be included in the transdermal delivery system to promote or potentiate permeation of the drug through the skin in order to achieve adequate serum levels for therapy.

Likewise, U.S. Pat. No. 4,668,232 provides an improved transdermal delivery system where drugs, including vasodilators, are present in a rubber and adhesive reservoir together with a water-swellable polymer to enhance permeation of the incorporated drug. The device can be used to administer calcium antagonists, with verapamil being exemplified.

U.S Pat. No. 4,690,683 specifically teaches a transdermal delivery device for administration of verapamil at a high rate of delivery. Verapamil, as a free base, is dispersed in an electroneutral lipophilic polymer matrix, e.g., a silicone elastomer. According to this patent, the verapamil should exist essentially in its electrically neutral non-ionic form (i.e., verapamil base) in order for the drug to be efficiently released from the polymer matrix (col. 4, lines 5-20). Enhancing agents, such as a saturated aliphatic alcohol, may be included in the delivery system to enhance permeation of the drug.

Nifedipine and other dihydropyridine calcium antagonists which have been incorporated into transdermal delivery systems are disclosed in Japanese applications, Derwent Nos. 61129140 and 58038213. These references also teach various enhancing agents to potentiate drug permeation.

Several references have disclosed transdermal devices for delivery of diltiazem. For example, European Patent Application No. 0159168 discloses a "soft patch"

device comprising a drug, a water soluble protein having an absorption promoting effect (i.e., a permeation enhancer), a polyhydric alcohol, a tackifier and an oleaginous substance. Numerous drugs, including diltiazem and other calcium antagonists, either in a non-ionized form or as an ionized acid or base addition salt form, can be used in the delivery system.

Transdermal delivery of diltiazem hydrochloride is also the subject of Japanese unexamined Patent Disclosure No. 132828-1987. The reference acknowledges the poor percutaneous absorption of diltiazem hydrochloride which is due to its hydrophilic nature and teaches that absorption of the drug may be enhanced by the inclusion of non-ionic water soluble macromolecules in the delivery system.

Recently, several new 8-chloro-1,5-benzothiazapine derivatives with calcium channel blocking activity have been described. A particularly promising drug with potent vasodilating activity for treatment of hypertension and angina is (+)(2S,3S)-3-acetoxy-8-chloro-5-(2-dimethylaminoethyl)-2,3-dihydro-2-(4-methoxyphenyl)-1,5-benzothiazepin-4-(5H)-one ("TA-3090"), exemplified in U.S. Pat. No. 4,567,175. However, a once-a-day oral dose of TA-3090 to achieve a sustained systemic therapeutic level does not appear to be feasible because of incomplete oral absorption and/or first pass metabolism of the drug by the liver.

SUMMARY OF THE INVENTION

A method for systemic administration of (+)(2S,3S)-3-acetoxy-8-chloro-5-(2-dimethylaminoethyl)-2,3-dihydro-2-(4-methoxyphenyl) -1,5-benzothiazepin-4-(5H)-one ("TA-3090") has been found. The method involves transdermally administering the free base form of TA-3090 to achieve systemic plasma levels of the drug in a patient to achieve an anti-convulsant, anti-angina or vasodilating effect. The invention particularly relates to a method for treating hypertension and/or angina and/or epilepsy by transdermally administering an effective amount of TA-3090 to a patient in need of such treatment.

DETAILED DESCRIPTION OF THE INVENTION

The present invention provides a method for administering the calcium channel antagonist compound (+)(2S,3S)-3-acetoxy-8-chloro-5-(2-dimethylaminoethyl)-2,3-dihydro-2-(4-methoxyphenyl) -1,5-benzothiazepin-4-(5H)-one (herein "TA-3090") to patients in need of calcium channel blocking effect. The method involves transdermally administering the free base form of TA-3090. In particular, the invention provides a method of treating hypertension, angina or epilepsy by transdermally administering TA-3090 to a patient in need of treatment. Treatment with TA-3090 relieves angina, reduces convulsions and causes vasodilation.

The term "transdermally" as used herein means administering TA-3090 to the skin of a patient for percutaneous passage of the drug into the systemic circulation of the patient. Skin sites for administration of TA-3090 include various anatomic regions, such as the abdomen, buttocks, forearm, chest, back, etc. TA-3090 is administered to the skin by affixing thereto a transdermal delivery device into which TA-3090 free base has been incorporated. One or several such devices can be applied to the skin of the patient as needed to achieve a desired therapeutically plasma level or clinical effect.

Transdermal delivery devices for administering TA-3090 can be prepared by incorporating TA-3090 free base into various polymeric reservoir matrix materials, including, inter alia, pressure sensitive acrylic, silicone, polyurethane, ethylene vinyl acetate copolymers, polyolefins, and rubber adhesive matrices, medical grade silicone fluids, and medical grade silicone elastomers, which are known in the art for forming reservoirs for transdermal delivery of drugs. Preferred delivery systems include the incorporation of TA-3090 free base into DuroTak® 80-1194 and DuroTak® 80-1054 acrylic pressure sensitive adhesives from National Starch and Chemical Corporation; or MSP# 111788 and MSP# 111888 acrylic pressure sensitive adhesives from 3M Company; or Gelva® GMS 737 and GMS 788 acrylic pressure sensitive adhesives from Monsanto; or BIO-PSA® 2920 and BIO-PSA® 2892 Silastic pressure sensitive adhesives from Dow Corning Corporation; or Silastic MDX4-4210 medical grade elastomer (silicone) from Dow Corning Corporation; or Ethylene vinyl acetate copolymers, available from DuPont or other suppliers.

TA-3090 may be obtained from Marion Laboratories, Inc. It may be prepared as described in U.S. Pat. No. 4,567,165.

The drug is incorporated into the polymers according to the manufacturer's directions to achieve a loading concentration of the drug of about 0.1 to 70% w/w for the acrylic and silicone pressure sensitive adhesive polymers and for ethylene vinyl acetate copolymers; and about 0.1 to 10% w/w for the silicone elastomer. In general, the free base form of TA-3090 can be incorporated in the above-mentioned matrices to a higher % w/w loading than the salt form of TA-3090. After loading the drug, the devices are cured (i.e., allowed to polymerize/dried) and may be formed into patches of any desired geometric shape (circular, rectangular, oval, square or any other conceivable shape) with any desired surface area ranging from 0.1 to 200 cm$^2$ for use.

The rate of administration of the free base of TA-3090 incorporated into the transdermal delivery device is about 0.6 to 29.62 mcg/cm$^2$/hr. The plasma concentration of TA-3090 achieved at 24 hours after the topical application of a transdermal delivery system containing TA-3090 is 75.6 ng/ml. Generally, the amount of TA-3090 free base incorporated into the transdermal delivery device will be sufficient to maintain a desired plasma level for eight to 168 hours, preferably at least 24 hours. Thus, a device need be applied only once a day to maintain a desired plasma level of TA-3090. In accordance with the invention, one or more such TA-3090 transdermal delivery devices may be applied to the skin simultaneously or sequentially, one after another at periodic intervals as needed to sustain therapeutic levels of the drug in a patient. It is well within the skill of a treating physician to determine the amount of TA-3090 to be administered transdermally to a given patient to achieve a desired clinical result, i.e., whether one or more devices need be applied to the patient.

TA-3090 free base has been shown to effectively permeate the skin in a mouse model of transdermal drug delivery. The model used is an in-vitro excised hairless mouse skin model which is known in the art. The permeation rates of TA-3090 through the excised skin were measured using a Franz diffusion cell. At a loading concentration of 50% w/w in DuroTak® 80-1054, 40% w/w in DuroTak® 80-1194, 50% w/w in Gelva® GMS 788, 60% w/w in Gelva® GMS 737, 30% w/w in 3M adhesive# MSP 111788, 50% w/w in 3M adhesive# MSP 111888, 30% w/w in BIO-PSA® X7-2892, 40% w/w in BIO-PSA® X7-2920, 30% w/w in Elvax® 460, and 3% w/w in Silastic MDX4-4210 elastomer, the permeation rates of TA-3090 free base were 19.7, 8.5, 17.3, 13.3, 29.62, 23.13, 16.6, 17.8, 15.56 and 14.1 mcg/cm$^2$/hr, respectively.

TA-3090 free base, incorporated in a transdermal delivery system, has also been shown to effectively permeate the skin of live hairless guinea pigs when applied on the intact skin surface. When incorporated at a loading of 30% w/w in adhesive# MSP 111788 (3M Company), a plasma concentration of 75.6 ng/ml of TA-3090 was achieved at 24 hour time point in hairless guinea pigs.

It is thus believed that the transdermal delivery of TA-3090 will be useful in maintaining a desired plasma level for a particular disease condition.

The invention is further illustrated by the following specific examples which are not intended in any way to limit the scope of the invention.

EXAMPLE 1

Fabrication of TA-3090 free base transdermal delivery system in a pressure sensitive adhesive reservoir The required amount of TA-3090 free base (to get a desired % w/w loading) is dissolved in the adhesive solution under very low agitation (to avoid air entrapment) and covered (to minimize solvent evaporation) conditions. Pressure sensitive adhesives are commercially available either as a solution of polymers in an organic blend or as an emulsion in water (emulsified with the aid of an emulsifier(s)). TA-3090 free base is usually soluble in these polymer/organic solvent solutions. If TA-3090 is not easily soluble in the adhesive solution (or in emulsion type pressure sensitive adhesive products where TA-3090 free base is not very soluble), it can be dissolved in a suitable solvent beforehand. The drug/adhesive solution blend is coated on a suitable release liner (one such commercially available product is 3M product# 1022, which is a polyester film coated with a fluoropolymer) to a desired thickness. The coated liner is then dried at a suitable temperature (in an oven, for example) for a length of time enough to drive off the residual solvents from the coated film. A substrate liner (examples of such commercially available products are 3M product# 1006, 1009, 1109, etc.) is then laminated onto this dried film. Patches of desired shape and surface area are cut from this coated web for further evaluation. The release liner is peeled off and discarded before use. The exposed drug/adhesive film is placed on the skin.

EXAMPLE 2

Method of preparation of the Silicone elastomer (Silastic) reservoir system containing TA-3090

The required amount of TA-3090 free base (to get a desired % w/w loading) is dissolved in a minimal volume of a suitable solvent, such as acetone, acetonitrile, methanol, ethanol, etc. The required amount of elastomer is then added to the dissolved free base and mixed well with a suitable mixer, such as a lightning mixer, to get a homogeneous blend. A curing agent (crosslinking agent) is then added and mixed well with the mixer. Vacuum is then applied to remove entrapped air. This mixture is then poured between two smooth stainless steel plates, separated to a desired thickness by shimms (spacer films of precise thickness). The elastomer/drug sheet is cured (polymerized) at room temperature. Curing can be accelerated by means of high temperature conditions. Patches of desired shape and dimensions can then be cut for further evaluation and use. Since these elastomeric matrices are usually not self-sticking, an adhesive coated overlay tape is needed to affix them on the skin. Alternatively, a thin film of a suitable pressure sensitive adhesive can be applied onto the elastomer to help it adhere to the skin.

EXAMPLE 3

Method of preparation of ethylene vinyl acetate copolymers (EVA) matrix containing TA-3090 free base The required amount of EVA resin, such as ELVAX® 460 (DuPont) which has a vinyl acetate content of 17.5-18.5%, is dissolved in a suitable solvent such as methylene chloride. For the purpose of present invention, any other suitable EVA resin with different vinyl acetate content can be used. The required amount of TA-3090 is then added and mixed well to form a uniform solution. This is then coated on a suitable laminate such as 3M product# 1022 which is a release liner. The coated film is then dried (air or in an oven at a suitable temperature) to drive off the residual solvent (methylene chloride or other). A substrate laminate, such as 3M product# 1006, is then laminated onto the dried film. Transdermal patches of any desired shape and dimension are cut for further evaluation and use.

EXAMPLE 4

In-vitro skin permeation determination using the Franz diffusion cell

In-vitro evaluation of transdermal patches was accomplished using an excised hairless mouse/Franz diffusion cell model (available from Crown Glass Company, Somerville, N.J.) as follows. Immediately following sacrifice by cervical dislocation (or by $CO_2$ gas), a portion (about 3.5 cm×3.5 cm) of the full-thickness abdominal skin was carefully excised from the hairless mouse (5-7 week old, male). The dermal side of the skin was carefully cleaned of any adhering subcutaneous tissue and/or blood vessels.

5% w/w Polyethylene glycol 20 Oleyl ether (Trycol-20 Oal®, Emery) in 0.9% w/w sodium chloride was used as the dermal elution medium in the receptor compartment of the Franz cell. The aqueous solubility of TA-3090 free base was improved by the incorporation of 5% PEG 20 Oleyl ether as a solubilizer to maintain an effective sink condition required in the investigation, which simulates the biological sink achieved by hemoperfusion. PEG 20 Oleyl ether was found not to affect the integrity or the permeability of the skin in a previously published study (R. L. Bronaugh and R. F. Stewart, J. Pharm. Sci., Vol. 73, No. 9, (1984), p 1255). Full-thickness skin prepared freshly as outlined above was mounted on the receptor compartment of the Franz diffusion cell with the stratum corneum side facing upward and the dermis side facing downward into the receptor compartment. A unit of transdermal patch was placed onto the skin with the drug-releasing side in intimate contact (slight pressure is applied) with the stratum corneum. The donor compartment was placed over the transdermal patch and the whole assembly was then securely clamped together. Following this, the saline solution containing 5% w/w PEG 20 Oleyl ether (Trycol ®) at 37° C. was introduced into the receptor compartment, which was thermostatically controlled at 37° C. by a circulating water bath. At the same time, the donor compartment was maintained at ambient temperature (24°±2° C.).

At a predetermined time interval (usually 4, 8, 12 and 24 hours), the entire volume of the receptor solution was withdrawn and immediately replaced with the same volume of the fresh, drug-free Trycol solution at 37° C. to maintain the sink condition. The concentration of TA-3090 in the sample was determined by a sensitive HPLC method. From the concentration profiles of TA-3090 in the receptor compartment, the flux (mcg/cm$^2$) of skin permeation was calculated using a computer program and then plotted as a function of time (hour). The slope of this line gave the value of skin permeation rate (mcg/cm$^2$/hr).

The results of these tests are set forth in Table I. Values are expressed as the mean and standard deviation of three observations.

TABLE I
In-vitro skin permeation of TA-3090

| Patch | Form of TA-3090 | Drug Loading (% w/w) | Skin Permeation Rate (mcg/cm$^2$/hr) |
|---|---|---|---|
| DuroTak ® 80-1194* adhesive patches | free base | 10% | 00.59 ± 0.12 |
| DuroTak ® 80-1194 adhesive patches | free base | 20% | 02.95 ± 0.56 |
| DuroTak ® 80-1194 adhesive patches | free base | 30% | 05.54 ± 0.28 |
| DuroTak ® 80-1194 adhesive patches | free base | 40% | 08.47 ± 0.46 |
| DuroTak ® 80-1194 adhesive patches | free base | 60% | 15.58 ± 2.87 |
| DuroTak ® 80-1194 adhesive patches | Maleate salt | 5% | 1.42 ± 0.48 |
| DuroTak ® 80-1194 adhesive patches | Maleate salt | 10% | 1.47 ± 0.14 |
| DuroTak ® 80-1054* adhesive patches | free base | 30% | 10.61 ± 0.42 |
| *National Starch & Chemicals | | | |
| DuroTak ® 80-1054 adhesive patches | free base | 40% | 15.09 ± 1.09 |
| DuroTak ® 80-1054 adhesive patches | free base | 50% | 19.69 ± 2.53 |
| DuroTak ® 80-1054 adhesive patches | free base | 60% | 16.14 ± 3.42 |
| DuroTak ® 80-1054 adhesive patches | Maleate salt | 10% | 00.00 ± 0.00 |
| DuroTak ® 80-1054 adhesive patches | Maleate salt | 20% | 00.00 ± 0.00 |
| Gelva ® GMS 788* adhesive patches | free base | 5% | 3.68 ± 0.76 |
| Gelva ® GMS 788 adhesive patches | free base | 10% | 8.53 ± 0.79 |
| Gelva ® GMS 788 adhesive patches | free base | 15% | 9.10 ± 1.54 |
| Gelva ® GMS 788 adhesive patches | free base | 30% | 16.56 ± 1.85 |
| Gelva ® GMS 788 adhesive patches | free base | 40% | 15.28 ± 2.07 |
| Gelva ® GMS 788 adhesive patches | free base | 50% | 17.29 ± 1.40 |
| Gelva ® GMS 788 adhesive patches | Maleate salt | 5% | 3.18 ± 0.12 |
| Gelva ® GMS 788 adhesive patches | Maleate salt | 15% | 1.60 ± 0.20 |
| Gelva ® GMS 788 adhesive patches *Monsanto | Maleate salt | 20% | 3.95 ± 0.15 |
| Gelva ® GMS 737* adhesive patches | free base | 5% | 2.06 ± 0.35 |
| Gelva ® GMS 737 adhesive patches | free base | 60% | 13.35 ± 0.77 |
| Gelva ® GMS 737 | Maleate | 20% | 2.63 ± 0.56 |
| adhesive patches | salt | | |
| Acrylate adhesive # MSP 111788** patches | free base | 15% | 18.17 ± 2.35 |
| Acrylate adhesive # MSP 111788 patches | free base | 20% | 22.54 ± 2.64 |
| Acrylate adhesive # MSP 111788 patches | free base | 30% | 29.62 ± 1.02 |
| Acrylate adhesive # MSP 111888 patches | free base | 30% | 16.26 ± 1.74 |
| Acrylate adhesive # MSP 111888 patches | free base | 40% | 21.65 ± 1.26 |
| Acrylate adhesive # MSP 111888 patches | free base | 50% | 23.13 ± 1.02 |
| X7-2892*** adhesive patches | free base | 5% | 9.10 ± 0.49 |
| X7-2892 adhesive patches | free base | 10% | 14.01 ± 0.96 |
| X7-2892 adhesive patches | free base | 30% | 16.58 ± 1.55 |
| X7-2892 adhesive patches | free base | 40% | 12.99 ± 9.85 |
| *Monsanto **3M Company ***Dow Corning | | | |
| X7-2892 adhesive patches | Maleate salt | 5% | 1.65 ± 0.12 |
| X7-2892 adhesive patches | Maleate salt | 10% | 1.71 ± 0.45 |
| X7-2920* adhesive patches | free base | 5% | 9.93 ± 1.28 |
| X7-2920 adhesive patches | free base | 10% | 14.14 ± 0.55 |
| X7-2920 adhesive patches | free base | 30% | 14.75 ± 1.01 |
| X7-2920 adhesive patches | free base | 40% | 17.80 ± 2.82 |
| X7-2920 adhesive patches | Maleate salt | 5% | 1.83 ± 0.52 |
| X7-2920 adhesive patches | Maleate salt | 10% | 2.09 ± 0.37 |
| Silastic matrix MDX4-4210* patches | free base | 1% | 10.40 ± 2.16 |
| Silastic matrix MDX4-4210 patches | free base | 2% | 11.30 ± 3.43 |
| Silastic matrix MDX4-4210 patches | free base | 3% | 14.13 ± 7.04 |
| Silastic matrix MDX4-4210 patches | free base | 4% | 12.75 ± 4.33 |
| Silastic matrix MDX4-4210 patches | Maleate salt | 1% | 0.70 ± 0.37 |
| Silastic matrix MDX4-4210 patches *Dow Corning | Maleate salt | 2% | 0.52 ± 0.17 |
| Elvax ® 460* patches | free base | 5% | 3.29 ± 0.88 |
| Elvax ® 460 patches | free base | 20% | 10.13 ± 0.97 |
| Elvax ® 460 patches | free base | 30% | 15.56 ± 1.25 |
| Elvax ® 460 patches | Maleate salt | 5% | 2.06 ± 0.18 |
| *DuPont | | | |

EXAMPLE 5

Intrinsic in-vitro skin permeability of TA-3090 at various pH conditions

TA-3090 skin permeability was determined using a freshly excised hairless mouse skin and a side-by-side type of diffusion cell (available from Crown Glass Co., Somerville, N.J.). About 2.5 cm×2.5 cm portion of freshly excised hairless mouse skin (5–7 week old, male), prepared as described in Example 4, was mounted between the two chambers of the side-by-side diffusion cell and securely clamped. Saturated solution (with some extra drug in suspension state) of TA-3090 free base in phosphate buffer solution maintained at a particular pH was introduced into the donor side (the side facing the stratum corneum). 5% Trycol ® solution in normal saline, prepared as described in Example 4, was introduced in the receptor compartment (the side facing the dermis side of the skin). Both donor and receptor compartments were maintained at 37° C. by a thermostatically controlled circulating water bath. At predetermined time intervals (usually at 3, 6, 12 and 24 hours) the entire volume of the receptor solution was withdrawn and immediately replaced with the same volume of the fresh, drug-free Trycol ® solution at 37° C. to maintain the sink condition. The concentration of TA-3090 in the sample was determined by a sensitive HPLC method. From the concentration profiles of TA-3090 in the receptor compartment, the flux (mcg/cm$^2$) of skin permeation was calculated using a computer program and then plotted as a function of time (hour). Slope of this line gave the value of skin permeation rate (mcg/cm$^2$/hr).

The results are set forth in Table II.

TABLE II

Effect of pH on the intrinsic skin permeability of TA-3090

| Donor side pH | Skin Permeation Rate (mcg/cm$^2$/hr) | Solubility of TA-3090 in donor solution (mg/ml) | Intrinsic Permeability* (cm/hr) × 10$^{-3}$ |
| --- | --- | --- | --- |
| 5 | 49.04 ± 8.76 | 7.73 ± 1.130 | 6.53 ± 2.1 |
| 7 | 29.39 ± 11.61 | 0.60 ± 0.020 | 48.40 ± 18.3 |
| 9 | 6.75 ± 1.54 | 0.06 ± 0.004 | 110.08 ± 27.3 |

Values are expressed as the mean and standard deviation of three observations.
*Intrinsic permeability = Skin permeation rate/solubility.

EXAMPLE 6

Transdermal bioavailability of TA-3090 in live hairless guinea pigs

Hairless guinea pigs weighing about 400 gm were used in this study. Each animal was housed in an individual cage at a controlled ambient temperature of 72°±4° F., and a relative humidity of 40% to 60%. Food and water were provided ad libitum. Transdermal patches, 58 cm$^2$ in size, containing 30% TA-3090 free base in adhesive# MSP 111788 (3M Company) were applied on the dorsal side of the body and secured well with surgical tape. Animals were then wrapped with adhesive elastic bandage to ensure a good and prolonged contact of the transdermal patches with the guinea pig body. Patches were left on the guinea pigs for up to 48 hours. Blood samples were collected at different time intervals up to 48 hours. Concentration of TA-3090 in the blood samples was determined by a sensitive HPLC method.

The results are set forth in Table III.

TABLE III

Plasma concentration profile of TA-3090 in hairless guinea pigs

| Drug Loading (% w/w) | Plasma concentration of TA-3090 (ng/ml) | | | |
| --- | --- | --- | --- | --- |
| | 4 hours | 8 hours | 24 hours | 48 hours |
| 30% w/w | 11.39 ± 4.09 | 32.54 ± 4.56 | 75.60 ± 9.17 | 71.07 ± 43.13 |

Values are expressed as the mean and standard deviation of experiments conducted in three guinea pigs.

EXAMPLE 7

Intrinsic in-vitro skin permeability of diltiazem

Using a freshly excised hairless mouse skin and a side-by-side type of diffusion cell (available from Crown Glass Co., Somerville, N.J.), the intrinsic in-vitro skin permeability of diltiazem (free base or hydrochloride salt) was determined. About 2.5 cm × 2.5 cm portion of freshly excised hairless mouse skin (5–7 week old, male) prepared as described in Example 4 above, was mounted between the two chambers of the side-by-side diffusion cell and securely clamped. Saturated solution (with some extra drug in suspension state) of diltiazem free base or hydrochloride salt in 5% Trycol ® solution in 0.9% sodium chloride was introduced into the donor side (the side facing the stratum corneum). 5% Trycol ® solution in normal saline, prepared as described in Example 4 above, was introduced into the receptor compartment (the side facing the dermis side of the skin). Both donor and receptor compartments were maintained at 37° C. by a thermostatically controlled circulating water bath. At predetermined time intervals (usually at 3, 6, 12 and 24 hours) the entire volume of the receptor solution was withdrawn and immediately replaced with the same volume of fresh, drug-free Trycol ® solution at 37° C. to maintain the skin condition. The concentration of diltiazem in the sample was determined by a sensitive HPLC method. From the concentration profiles of diltiazem in the receptor compartment, the flux (mcg/cm$^2$) of skin permeation was calculated using a computer program and then plotted as a function of time (hour). Slope of this line gave the value of skin permeation rate (mcg/cm$^2$/hr).

The results are set forth in Table IV.

TABLE IV

Determination of intrinsic skin permeability of diltiazem

| Donor side species | Skin permeation rate (mcg/cm$^2$/hr) | Solubility of diltiazem HCl in donor solution (mg/ml) | Intrinsic Permeability* (cm/hr) × 10$^{-5}$ |
| --- | --- | --- | --- |
| Salt | 6.20 ± 1.58 | 373.98 ± 3.55 | 1.66 ± 0.43 |
| Free Base | 7.72 ± 2.01 | 4.13 ± 0.02 | 186.96 ± 49.74 |

Values are expressed as the mean and standard deviation of three observations.
*Intrinsic permeability = Skin permeation rate/solubility.

What is claimed is:

1. A method for treating angina, epilepsy or hypertension comprising transdermally administering to a patient suffering from angina, epilepsy or hypertension the compound (+)(2S,3S)-3-acetoxy-8-chloro-5-(2-dimethylaminoethyl)-2,3-dihydro-2-(4-methoxyphenyl)-1,5-benzothiazepin-4-(5H)-one in an amount sufficient to achieve a systemic vasodilating, anti-angina or anti-convulsant effect wherein a plasma concentration of 75.6 ng/ml of the compound is achieved.

2. Method according to claim 1 wherein the compound is administered at a transdermal permeation rate of about 0.59 to 29.62 mcg/cm$^2$/hr.

3. A delivery device for sustained transdermal administration of the compound (+)(2S,3S)-3-acetoxy-8-chloro-5-(2-dimethylaminoethyl)-2,3-dihydro-2-(4-methoxyphenyl)-1,5-benzothiazepin-4-(5H)-one to a patient in need of vasodilation, anti-angina or anti-convulsant effect, comprising a polymeric reservoir matrix in which the compound is incorporated in an amount sufficient to transdermally permeate the skin and achieve effective plasma levels of 75.6 ng/ml when affixed to a patient's skin.

4. A method for treating angina, epilepsy or hypertension comprising transdermally administering to a patient suffering from angina, epilepsy or hypertension the compound (+) (2S,3S)-3-acetoxy-8-chloro-5-(2-dimethylaminoethyl)-2,3-dihydro-2-(4-methoxyphenyl)-1,5-benzothiazepin-4-(5H)-one in an amount sufficient to achieve a systemic vasodilating, anti-angina or anti-convulsant effect without a permeation enhancer, wherein a plasma concentration of 75.6 ng/ml of the compound is achieved.

5. The delivery device of claim 3 consisting of a polymeric reservoir matrix in which the compound is incorporated in an amount sufficient to transdermally permeate the skin and achieve effective plasma levels when affixed to a patient's skin.

* * * * *